United States Patent
Noe et al.

(10) Patent No.: US 8,273,938 B2
(45) Date of Patent: Sep. 25, 2012

(54) HEAVY OLEFIN PRODUCTION PROCESS

(75) Inventors: Robert J. L. Noe, Mount Prospect, IL (US); Stephen W. Sohn, Arlington Heights, IL (US); Jeffrey L. Pieper, Des Plaines, IL (US); Douglas G. Stewart, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/154,602

(22) Filed: Jun. 7, 2011

(65) Prior Publication Data

US 2011/0282125 A1     Nov. 17, 2011

Related U.S. Application Data

(63) Continuation-in-part of application No. 12/272,151, filed on Nov. 17, 2008, now Pat. No. 7,960,601.

(51) Int. Cl.
*C07C 7/12* (2006.01)
(52) U.S. Cl. ........ 585/822; 585/802; 585/820; 585/825; 585/827; 585/829; 585/654
(58) Field of Classification Search .................. None
See application file for complete search history.

(56) References Cited

U.S. PATENT DOCUMENTS

| | | | |
|---|---|---|---|
| 5,510,564 A | 4/1996 | Raghuram | |
| 6,106,702 A | 8/2000 | Sohn | |
| 6,395,950 B1 | 5/2002 | Rice | |
| 6,407,301 B1 * | 6/2002 | Foley et al. | 585/650 |
| 6,407,303 B1 | 6/2002 | O'Brien | |
| 6,552,242 B1 | 4/2003 | Rice | |
| 6,670,519 B1 | 12/2003 | Sohn | |
| 7,960,601 B2 * | 6/2011 | Noe et al. | 585/822 |

* cited by examiner

*Primary Examiner* — Tam M Nguyen
(74) *Attorney, Agent, or Firm* — Arthur E Gooding

(57) ABSTRACT

A process is presented for the selective separation and recovery of large normal paraffins from a heavy kerosene boiling point fraction. The process includes passing the heavy kerosene fraction through an adsorption separation system for separating the normal paraffins from the paraffin mixture. The recovered extract and raffinate streams are mixed with a diluent made up of a lighter hydrocarbon. The subsequent diluted extract and raffinate streams are passed through first fractionation columns to separate the desorbent from the diluent and the heavier paraffins. The mixture of the diluent and heavier paraffins is passed through a second set of fractionation columns to separate the diluent and the heavier paraffins.

19 Claims, 1 Drawing Sheet

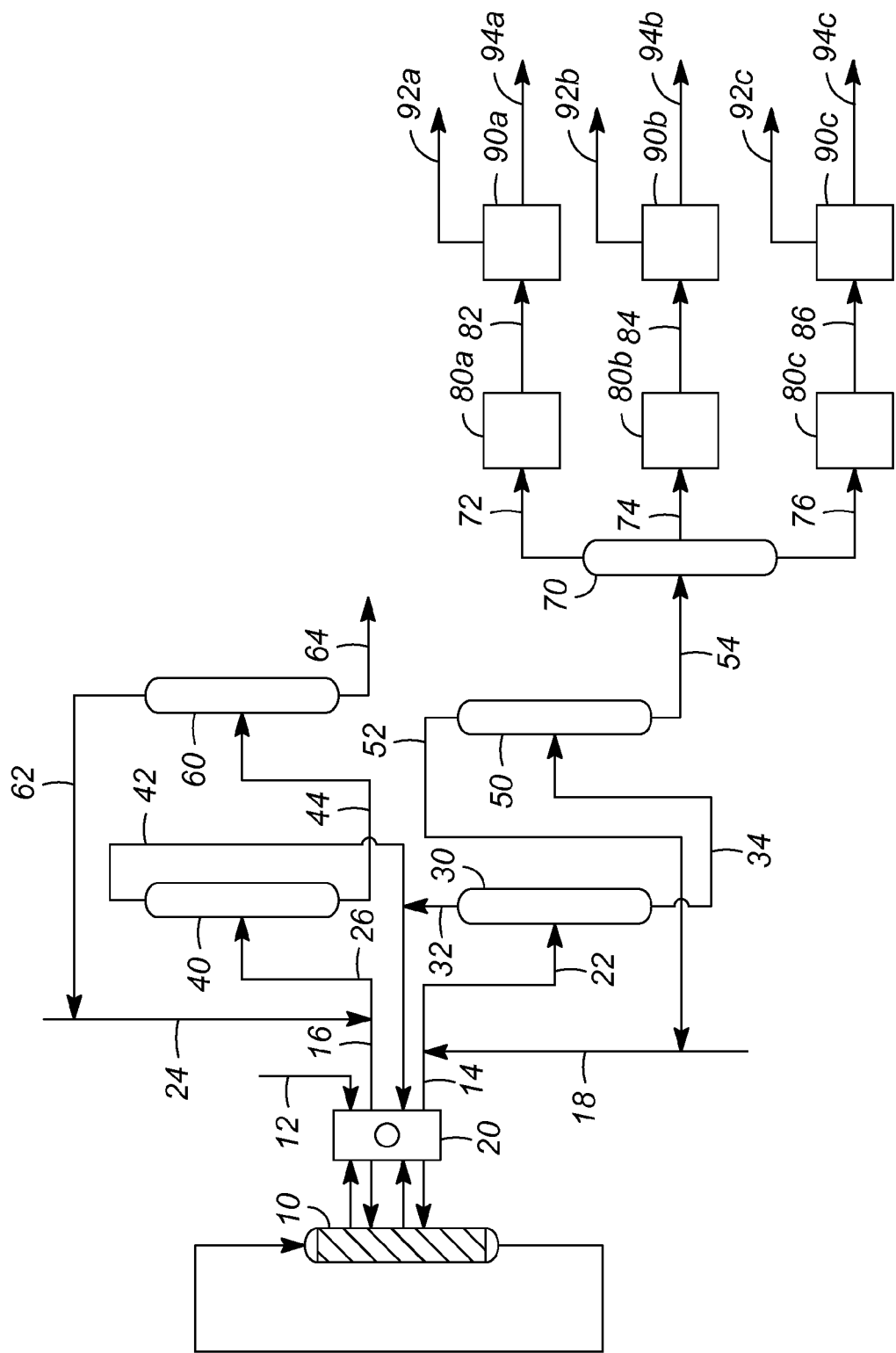

HEAVY OLEFIN PRODUCTION PROCESS

CROSS-REFERENCE TO RELATED APPLICATIONS

This application is a continuation-in-part of U.S. application Ser. No. 12/272,151 filed Nov. 17, 2008, the entire contents of which are hereby incorporated by reference.

FIELD OF THE INVENTION

This invention relates to the separation of lightly branched and normal paraffins from a hydrocarbon mixture and the formation of larger olefins. Specifically, the separation is of larger lightly branched and normal paraffins from a heavy hydrocarbon mixture to form olefins, which requires a combination of adsorption separation and distillation.

BACKGROUND OF THE INVENTION

The production of normal paraffins provides the ability of upgrading products from straight runs of hydrocarbon streams derived from crude oil fractionation. In particular, straight run kerosene is further processed to separate out normal paraffins for higher valued products, such as used in the production of linear alkyl benzenes (LAB). Normal paraffins in the range of C10 to C13 are important precursors to LAB production, which is in turn used to produce linear alkyl benzene sulfonate (LAS). LAS is the predominant surfactant used in the production of detergents.

The large utility of detergents and other cleaners has led to extensive development in the areas of detergent production and formulation. While detergents can be formulated from a wide variety of different compounds much of the world's supply is formulated from chemicals derived from alkylbenzenes. The compounds are produced in petrochemical complexes in which an aromatic hydrocarbon, typically benzene, is alkylated with an olefin of the desired structure and carbon number for the side chain. Typically the olefin is actually a mixture of different olefins forming a homologous series having a range of three to five carbon numbers. The olefin(s) can be derived from several alternative sources. For instance, they can be derived from the oligomerization of propylene or butenes or from the polymerization of ethylene. Economics has led to the production of olefins by the dehydrogenation of the corresponding paraffin being the preferred route to produce the olefin.

The choice of carbon numbers is set by the boiling point range of straight run cuts from crude distillation. Kerosene boiling range fractions from crude oil provide heavier paraffins. Paraffins having 8 to 15 carbons are present in significant concentrations in relatively low cost kerosene. These paraffins have been a predominant source for linear alkanes and the leading source of olefin precursors for use in making LABs. Recovery of the desired normal paraffins from kerosene is performed by adsorption separation, which is one process in overall production of LABs. The paraffins are then passed through a catalytic dehydrogenation zone wherein some of the paraffins are converted to olefins. The resultant mixture of paraffins and olefins is then passed into an alkylation zone in which the olefins are reacted with the aromatic substrate. This overall flow is shown in U.S. Pat. No. 5,276,231, which is incorporated by reference in its entirety, directed to an improvement related to the adsorptive separation of byproduct aromatic hydrocarbons from the dehydrogenation zone effluent. PCT International Publication WO 99/07656 indicates that paraffins used in this overall process may be recovered through the use of two adsorptive separation zones in series, with one zone producing normal paraffins and another producing mono-methyl paraffins.

Adsorptive separation on a large scale does not allow for the moving of the adsorption bed, therefore the technology uses simulated moving bed technology. The simulation of a moving adsorbent bed is described in U.S. Pat. No. 2,985,589 (Broughton et al.), which is incorporated by reference in its entirety. The success of a particular adsorptive separation is determined by many factors. Predominant among these are the composition of the adsorbent (stationary phase) and desorbent (mobile phase) employed in the process. The remaining factors are basically related to process conditions, which are very important to successful commercial operation.

While adsorption separation technology allows for the separation of normal paraffins from a hydrocarbon mixture, there are problems in recovering higher molecular weight paraffins after the separation that currently limit the ability to recover higher molecular weight normal paraffins.

SUMMARY OF THE INVENTION

The present invention provides a process to recover normal and lightly branched olefins from a heavy cut of the kerosene or diesel boiling fraction that was generated in the course of dehydrogenation of a feedstock consisting primarily of normal and lightly branched paraffins. The process comprises using an adsorption separation unit to separate normal and lightly branched olefins in the C15 to C28 range from the remainder of the heavy kerosene or diesel. The normal and lightly branched olefins are passed out in an extract stream which includes the desorbent. The remainder is passed out in a raffinate stream, which also includes the desorbent. The extract stream is mixed with a diluent, thereby creating an intermediate extract stream. The intermediate extract stream is passed to a first fractionation column. The diluent provides for an intermediate boiling point liquid to allow the operation of the first fractionation column at a temperature low enough to prevent cracking of the normal and lightly branched olefins. The first fractionation column creates an overhead stream comprising the desorbent, and an intermediate extract bottoms stream comprising the normal and lightly branched olefins and the diluent. The raffinate stream is mixed with the diluent, creating an intermediate raffinate stream, and passed to a second fractionation column, that is operated at a temperature low enough to prevent cracking of the larger hydrocarbons in the intermediate raffinate stream. The second fractionation column has an overhead stream comprising the desorbent and an intermediate raffinate bottoms stream comprising the heavy hydrocarbons and the diluent.

The intermediate extract bottoms stream is passed to a third fractionation column, which is operated at below atmospheric pressure to allow boiling of the normal and lightly branched olefins at a temperature below cracking temperatures. The third fractionation column has an overhead comprising the diluent, and a bottoms stream comprising the normal and lightly branched olefins in the C15 to C28 range.

The intermediate raffinate bottoms stream is passed to a fourth fractionation column, which is operated below atmospheric pressure to allow boiling of the heavy hydrocarbons at a temperature below cracking temperatures. The fourth fractionation column has an overhead comprising the diluent, and a bottoms stream comprising the heavy hydrocarbons separated from the normal paraffins.

The process provides for the recovery of normal and lightly branched olefins from a heavy hydrocarbon stream, while allowing separation and recovery of the desorbent at temperatures sufficiently low to prevent the destruction through cracking of the desired product stream of normal and lightly branched olefins. The desorbent and diluent are recovered and recycled in this process.

Additional objects, embodiments and details of this invention can be obtained from the following drawing and detailed description of the invention.

BRIEF DESCRIPTION OF THE DRAWING

FIGURE is a diagram of the present invention.

DETAILED DESCRIPTION OF THE INVENTION

The recovery of higher molecular weight paraffins from the kerosene fraction presents many problems. In particular, the recovery of normal paraffins in the C15 to C19 range presents several conflicting problems. The feedstock of choice is a heavy cut from the kerosene boiling fraction. The extract stream from an adsorption separation unit will contain the normal paraffins, and the desorbent from the process. The current recovery of the normal paraffins in the C8 to C14 range from the extract mixture containing the desorbent and the normal paraffins is to fractionate the mixture. The desorbent is recovered in the fractionation column overhead, while the normal paraffins are recovered from column bottoms. With higher molecular weight paraffins in order to separate the paraffins from the desorbent, sufficient heat must be applied to boil the normal paraffins. However, at those temperatures the normal paraffins will crack, and will render the separation process ineffective. If the fractionation is performed under a vacuum, in order to reduce the temperature of operation, then the desorbent can not be condensed in a manner that does not require expensive technology, such as a significant refrigeration system.

In addition, large olefins, i.e. olefins having 10 or more carbons, were used for a variety of purposes. One important purpose was the development of detergents and surfactants. However, it was found that olefins that were highly branched presented problems. Highly branched olefins were typically highly branched, and were characterized by a large portion of the aliphatic carbon chain is in at least one branch and more commonly in three or more alkyl group branches. Thus, the branched olefins have a relatively large number of primary carbon atoms per aliphatic alkyl group. Another characteristic of highly branched olefins is that the double bond is not on the second carbon atom of the longest chain, but is distributed among the branched olefins at different positions. When alkylating highly branched olefins with benzene, a low selectivity to 2-phenyl alkanes is obtained with a selectivity of 2-phenyl alkanes typically between 10 and 40. Another characteristic of highly branched olefins is the presence of internal quaternary carbon atoms, with the proportion of internal quaternary carbon atoms near 10 mol % of the carbons.

It has been found that, while linear alkylbenzenes are best for a variety of applications, modified alkylbenzenes can in many instances be quite effective. Modified alkylbenzenes are formed from benzene alkylated with lightly branched olefins. Therefore, it has been found that separating out lightly branched olefins from highly branched olefins is an important aspect for increasing the available stock of useful olefins. The characteristics of lightly branched olefins include the number of primary carbon atoms as between that of highly branched olefins and linear olefins. Another characteristic of lightly branched olefins is that a high proportion of the olefins have the double bond on the second carbon atom and that the proportion will be between 40 and 100 percent. A third characteristic of lightly branched olefins is the low proportion of internal quaternary carbon atoms.

The lightly branched monoolefin may be an alpha monoolefin or a vinylidene monoolefin, but is normally an internal monoolefin. As used herein, the term "alpha olefins" refers to olefins having the chemical formula, R—CH═CH2. The term "internal olefins," as used herein, includes di-substituted internal olefins having the chemical formula R—CH═CH—R; tri-substituted internal olefins having the chemical formula R—C(R)═CH—R; and tetra-substituted olefins having the chemical formula R—C(R)═C(R)—R. The di-substituted internal olefins include beta internal olefins having the chemical formula R—CH═CH—CH3. As used herein, the term "vinylidene olefins" refers to olefins having the chemical formula R C(R)═CH2. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond.

The lightly branched olefins can include having two or more branches, but preferably, the lightly branched olefins comprises a mixture that includes monomethyl, dimethyl, monoethyl, and monopropyl olefins with a small amount of olefins having larger branches or more branches. Generally, it is preferred that the lightly branched olefins comprise at least 70 mol % of the olefins in the mixture with a more preferred composition comprising at least 85 mol % of the olefins in the mixture. Monoolefins having either two alkyl group branches or four primary carbon atoms and a quaternary carbon atom comprise generally less than 10 mol-%, and preferably less than about 1 mol-%, of the total lightly branched monoolefins in the mixture.

The present invention provides for overcoming these two competing drawbacks. The process comprises adding a diluent to the extract and raffinate streams leaving the adsorption separation unit. The extract and raffinate streams are then fractionated to separate the desorbent from the extract and raffinate streams, and then pass the remaining mixtures to a fractionation system operated at low pressure and temperature to separate the diluent from the extract and raffinate streams.

In particular, the process for producing a heavy paraffin product stream from a hydrocarbon feedstream is shown in the FIGURE. The process comprises passing the hydrocarbon feedstream 12 to an adsorption separation unit 10. The adsorbent chosen will have pore sizes to allow for lightly branched paraffins, as well as n-paraffins. The hydrocarbon feedstream 12 is selected for its content of normal and lightly branched paraffins in the C15 to C28 range. The adsorption separation unit 10 creates an extract stream 14 comprising normal and lightly branched paraffins in the C15-C28 range and a desorbent. The adsorption separation unit 10 also creates a raffinate stream 16 comprising non-normal paraffins and the desorbent. The non-normal paraffins will comprise, generally, highly branched paraffins, and for convenience the use of the term non-normal paraffins will refer to highly branched paraffins. The extract stream 14 is mixed with a diluent 18, thereby creating an intermediate extract stream 22, and the raffinate stream 16 is mixed with the diluent 24, thereby creating an intermediate raffinate stream 26. The adsorption separation unit 10 has as a part of the system a rotary valve system 20 which controls the positions of the inflows to and outflows from the adsorption separation unit 10.

In addition, the adsorption separation system includes a flush zone. The flush zone is buffer zone, that moves through the system like the other zones, and is between the adsorption zone and the desorption zone. The flush zone clears out the material from the feed stream that has not been adsorbed before the desorbent zone passes. It also keeps the desorbent from breaking through to the adsorption zone, where if the desorbent were to break through to the adsorption zone, the process would experience a loss of the lightly branched and normal paraffin product. The flush zone has a hydrocarbon that will not displace the adsorbed material while it is displacing the non-adsorbed portion of the hydrocarbon feedstream. The flush zone hydrocarbon will preferably be an intermediate non-normal hydrocarbon, such as isooctane, or an aromatic compound in the C8 to C10 range, but can also comprise non-normal hydrocarbons outside the C8 to C10 range and can include naphthenes and aromatics. Examples of flush zone streams include isooctane and mixtures of isooctane and xylenes. One such mixture is a 70/30 mixture of isooctane and p-xylene.

The intermediate extract stream 22 is passed to a first separation column 30, which is operated at desorbent separation conditions to create a first column overhead stream 32 comprising the desorbent. The first separation column 30 also has a first column bottoms stream 34 comprising the normal and lightly branched paraffins in the C15-C28 range and the diluent. The first column bottoms, or intermediate extract bottoms, stream 34 is passed to a third column 50, which is operated at diluent separation conditions. The third column 50 has a third column overhead stream 52 comprising the diluent. The third column 50 also produces a third column bottoms stream 54 comprising normal and lightly branched paraffins in the C15-C28 range, which is the product stream.

The intermediate raffinate stream 26 is passed to a second separation column 40, which is operated at desorbent separation conditions to create a second column overhead stream 42 comprising the desorbent. The second separation column 40 also has a second column bottoms stream 44 comprising the non-normal paraffins and the diluent. The, second column bottoms, or intermediate raffinate bottoms, stream 44 is passed to a fourth column 60 which is operated at diluent separation conditions. The fourth column 60 has a fourth column overhead stream 62 comprising the diluent. The fourth column 60 also produces a fourth column bottoms stream 64 comprising non-normal paraffins in the C15-C28 range, and which is passed to other processing units in a petrochemical plant.

The columns 30, 40, 50, 60 are fractionation columns, and operating conditions include operating at temperatures and pressures to boil, or vaporize, the liquid at the bottom of the column to create an upflowing vapor stream, and to condense the vapor at the top of the column to create a downflowing liquid stream.

The process further comprises passing the third column bottoms stream 54 to a paraffin stream separation unit 70. The paraffin stream separation unit 70 separates the lightly branched and normal paraffins in the bottoms stream 54 into three streams: a first paraffin stream 72 comprising C15 to C19 lightly branched and normal paraffins; a second paraffin stream 74 comprising C20 to C23 lightly branched and normal paraffins; and a third paraffin stream 76 comprising C24 to C28 lightly branched and normal paraffins. The three paraffin streams 72, 74, 76 are passed to a dehydrogenation unit 80a, 80b, 80c to convert the paraffins to olefins, generating a first olefin stream 82 comprising C15 to C19 lightly branched and normal olefins, a second olefin stream 84 comprising C20 to C23 lightly branched and normal olefins, and a third olefin stream 86 comprising C24 to C28 lightly branched and normal olefins. Each stream can be sent to a separate dehydrogenation unit 80a, 80b, 80c, or the process can be controlled to send each paraffin stream to a single dehydrogenation unit 80, where each stream is sent separately, and the dehydrogenation unit 80 operating conditions are adjusted to accommodate the different feeds.

The paraffin separation unit 70 can comprise a fractionation system for generating the three paraffin streams, 72, 74, 76, and can include a single divided wall column or a pair of columns. The separation of the heavy paraffins into smaller ranges of molecular weight distributions facilitates the dehydrogenation process. The dehydrogenation process of paraffins operates best when the paraffins have a relatively narrow range of molecular weights, or a more limited carbon number range. The heavy paraffin stream is therefore divided into three streams having narrower ranges of carbon numbers.

The olefin streams 82, 84, 86 leaving the dehydrogenation unit 80a, 80b, 80c, are passed to an olefins separation unit 90 to generate an olefins stream 92 and a paraffins stream 94 comprising the unconverted paraffins. The olefins separation unit 90 can be a single separation unit, or each olefins stream 82, 84, 86 can be passed to a separate olefins separation unit 90a, 90b, 90c. The olefins separation unit 90 can comprise a second adsorption separation system, wherein an extract stream 92 comprises the olefins and a raffinate stream 94 comprises the unconverted paraffins. The functions and properties of adsorbents and desorbents in the chromatographic separation of liquid components are well-known, and reference may be made to U.S. Pat. No. 4,642,397, which is incorporated herein, for additional description of these adsorption fundamentals. An adsorbent for the second adsorption separation column comprises silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," Nature, Vol. 271, Feb. 9, 1978 which is incorporated herein by reference for its description and characterization of silicalite. Silicalite is a hydrophobic crystalline silica molecular sieve having an MFI type structure of intersecting bent-orthogonal channels formed with two cross-sectional geometries, 6 Å circular and 5.1-5.7 Å elliptical on the major axis. This gives silicalite great selectivity as a size selective molecular sieve. Another adsorbent, and a preferred adsorbent, is NaX zeolite. NaX has good adsorptive properties for olefins in an olefin/paraffin mixture.

The process of olefins separation from the paraffins in the olefins process streams 82, 84, 86 uses an adsorption-separation process to generate the olefins product streams 92a, b, c, and the raffinate streams 94a, b, c. The process uses a second desorbent to displace the selectively adsorbed material from the adsorbent. The desorbent is selected from a lighter hydrocarbon, preferably in the C5 to C8 range, that readily facilitates desorbing the adsorbed material. One preferred desorbent for the second desorbent is mixture of C6 compounds, and in particular a mixture of normal hexane and normal hexene. The extract streams 92a,b,c, and the raffinate streams 94a,b,c include desorbent with the materials being separated.

The extract streams, and the raffinate streams contain material, the desorbent, that presents the same problem as described above regarding the separation of lightly branched and normal paraffins from highly branched non-normal paraffins in the paraffin feedstock. The higher molecular weight paraffins and olefins need to be separated from the desorbent, and this process is now completed by repeating the above procedure to separate the low molecular weight desorbent from the high molecular weight olefins and paraffins. To each extract 92a,b,c, and raffinate 94a,b,c, stream a diluent is added after leaving the adsorption separation unit 90a,b,c. The diluents comprises an intermediate boiling point liquid. The extract and raffinate streams are then fractionated to separate the desorbent from the extract and raffinate streams, and then pass the remaining mixtures to a fractionation system operated at low pressure and temperature to separate the diluent from the extract and raffinate streams, thus allowing for separation at sufficiently low temperatures to prevent cracking of the desired product streams. Depending on the size, and throughput, of the hydrocarbons, the fractionation systems can be separate, or there can be a single system with storage for processing the different streams.

The normal operation of a fractionation column can be at atmospheric pressure or higher, but where the temperatures required to perform the fractionation are too great, the pressure can be reduced to below atmospheric. The operation of the first and second separation columns 30, 40 are operated at or above atmospheric conditions. These conditions allow for the condensation of the desorbent during the separation process. The operating conditions include temperatures between 35° C. and 300° C., and pressures between 100 kPa and 500 kPa. Considerations include the ability to condense the desorbent to create a reflux stream, and to boil the other components to create a vapor stream flowing upward from the bottom of the columns. The temperature must be kept sufficiently low as to prevent thermal cracking of the larger hydrocarbon paraffins.

The larger hydrocarbon olefins and paraffins, in the C15-C28 range require much higher temperatures to vaporize at atmospheric conditions, or above. The third and fourth separation columns 50, 60 are operated at lower pressures to allow the boiling of larger hydrocarbons at lower temperatures. The operating conditions allow for the condensation of the diluent during the separation process. The operating conditions include temperatures between 35° C. and 300° C., and pressures between 10 kPa and 100 kPa.

In a preferred embodiment, the invention seeks to obtain normal and lightly branched paraffins in a more narrow range. The preferred range is for normal and lightly branched paraffins in the C15 to C19 range, and the extract stream 14 will comprise normal paraffins in the C15 to C19 range with the desorbent. When the desorbent is separated from the normal paraffins, the product stream will comprise a normal and lightly branched paraffin mixture with properties listed in table 1.

TABLE 1

Properties of normal paraffin product stream

| | |
|---|---|
| sulfur content (μg/g) | ≦3 |
| bromine index (mgBr/100 g) | ≦25 |
| Saybolt color | +30 |
| aromatic mass fraction (%) | ≦0.4 |
| average molecular weight | 240-245 |
| normal and lightly branched paraffin content (mass frac. %) | ≧98.5 |
| C15 and below (mass frac. %) | ≦0.5 |
| C20 and above (mass frac. %) | ≦0.5 |

The diluent is provided to enable separation in the first and second fractionation columns 30, 40 at temperatures that will not thermally crack the paraffins in the extract or the raffinate streams. A preferred diluent comprises a hydrocarbon mixture of intermediate range paraffins having carbons in the C10 to C14 range. An alternate diluent can comprise aromatic compounds, or a mixture of aromatic compounds and lighter paraffins in the C8 to C10 range, or lighter paraffins. One choice of diluent is an aromatic mixture comprising xylenes, and in particular paraxylene. Another choice of diluent includes isooctane.

The desorbent for the adsorption separation process preferably comprises paraffins in the C5 to C8 range. The smaller paraffins readily displace the larger normal paraffins during the desorption stage of the adsorption separation process. Preferably the lighter paraffins are normal paraffins. One preferred desorbent is n-pentane or n-hexane. Mixtures of light paraffins are also preferred, and mixtures include a light normal paraffin with isooctane. Such mixtures include a desorbent such as n-pentane and isooctane, or n-hexane and isooctane. The desorbent recovered in the first and second fractionation columns 30, 40 can be recycled and passed back to the adsorption separation unit 10.

The preferred desorbent is a mixture of a light normal paraffin and an intermediate non-normal paraffin, such as n-pentane and isooctane. The normal paraffin is used to displace the adsorbed large normal paraffin extracted from the hydrocarbon feedstream 12 in the adsorption separation unit 10. A mixture is preferred utilizing a larger non-normal paraffin to minimize the chamber pressure of the adsorption separation unit 10. The mixture comprises a normal paraffin content between 1 wt % and 99 wt % with the remainder comprising a non-normal paraffin. In one preferred mixture, the composition is a 60/40 mix of a normal paraffin, such as n-pentane or n-hexane, and a branched paraffin such as isooctane.

In addition to the continuous adsorption separation system normally contemplated, other adsorption separation system processes are also applicable for use in the present invention, and it is intended that the invention covers other adsorption separation systems. One such system can be found in U.S. Pat. Nos. 3,422,005 (W. F. Avery) and 4,350,593 (Andrija Fuderer) which are incorporated by reference in their entirety. This process comprises passing a hydrocarbon feedstream having normal paraffins over an adsorbent at isobarometric conditions. The normal and lightly branched paraffins are allowed to adsorb, and the adsorption step is followed by a purge step, typically flowing a normal paraffin, such as n-hexane, in a co-current manner to purge the adsorption chamber of the non-normal hydrocarbons. The purge step is followed by a desorption step where a desorbent is flowed counter-currently to desorb the normal paraffins, thereby creating an extract stream comprising normal paraffins and the desorbent, which is then further processed as described above.

In another embodiment, the invention further comprises passing the recovered diluent back into the process. The third column overhead stream 52 can be recycled and passed back to be mixed with the extract stream 14. The overhead stream 52 can be mixed with additional diluent to form the stream 18 that is mixed with the extract stream 14 to make up for diluent lost to other process streams. The fourth column overhead stream 62 can be recycled and passed back to be mixed with the raffinate stream 16. The overhead stream 62 can be mixed with makeup diluent to form the diluent stream 24 which is mixed with the raffinate stream 16. In an alternative, the two recovered diluent streams 52, 62, can be mixed prior to mixing with the extract stream 14 or the raffinate stream 16. This depends on the losses and relative amounts needed for performing the separations.

The severity of separation of the desorbent from either or both the extract stream and the raffinate stream can require subsequent separation. The overhead streams from the first and second columns 30, 40 can comprise a mixture of the desorbent and the diluent. The desorbent can require further processing for obtaining a sufficiently pure desorbent for the adsorption separation unit 10. The overhead streams 32, 42 from the first and second columns 30, 40 be collected passed to a fifth separation column (not shown). The fifth separation column can further separate the mixture into a fifth column overhead stream comprising a light hydrocarbon, or the desorbent. The fifth separation column can further produce a bottoms stream comprising an intermediate hydrocarbon, or the diluent.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for producing a heavy olefin product stream, comprising:
    passing a hydrocarbon feedstream comprising paraffins in the C15-C28 range to an adsorption separation unit, thereby creating an extract stream, comprising normal and lightly branched paraffins in the C15-C28 range and a first desorbent and a raffinate stream, comprising non normal paraffins in the C15-C28 range and a first desorbent;
    mixing the extract stream with a diluent, thereby creating an intermediate extract stream;
    mixing the raffinate stream with a diluent, thereby creating an intermediate raffinate stream;
    passing the intermediate extract stream to a first separation column operated at first desorbent separation conditions, thereby creating first column overhead stream comprising the first desorbent, and a first column bottoms stream comprising the normal and lightly branched paraffins in the C15-C28 range and the diluent;
    passing the intermediate raffinate stream to a second separation column operated at first desorbent separation conditions, thereby creating a second column overhead stream comprising the first desorbent, and a second column bottoms stream comprising non-normal paraffins and the diluent;
    passing the first column bottoms stream to a third separation column operated at diluent separation conditions, thereby creating a third column overhead stream comprising the diluent, and a third column bottoms stream comprising the normal and lightly branched paraffins in the C15-C28 range;
    passing the second column bottoms stream to a fourth separation column operated at diluent separation conditions, thereby creating a fourth column overhead stream comprising diluent, and a fourth column bottoms stream comprising non-normal paraffins;
    passing the third column bottoms stream to a paraffin stream separation unit to create a first paraffin stream comprising C15 to C19 lightly branched paraffins, a second paraffin stream comprising C20 to C23 lightly branched paraffins, and a third paraffin stream comprising C24 to C28 branched paraffins; and
    passing the first paraffin stream to a dehydrogenation unit to generate a first effluent stream comprising C15 to C19 lightly branched olefins and unconverted paraffins;
    passing the second paraffin stream to the dehydrogenation unit to generate a second effluent stream comprising C20 to C23 lightly branched olefins and unconverted paraffins; and
    passing the third paraffin stream to the dehydrogenation unit to generate a third effluent stream comprising C24 to C28 lightly branched olefins and unconverted paraffins.

2. The process of claim 1 wherein the paraffin stream separation unit comprises a fractionation system.

3. The process of claim 1 further comprising passing the first effluent stream to the second adsorption separation unit thereby creating a C15 extract stream comprising C15 to C19 olefins and a C15 to C19 raffinate stream comprising paraffins.

4. The process of claim 1 further comprising passing the first effluent stream to the second adsorption separation unit thereby creating C20 extract stream comprising C20 to C23 olefins and a C20 to C23 raffinate stream comprising paraffins.

5. The process of claim 1 further comprising passing the first effluent stream to the second adsorption separation unit thereby creating a C24 extract stream comprising C24 to C28 olefins and a C24 to C28 raffinate stream comprising paraffins.

6. The process of claim 1 wherein the diluent recovered from the third separation column is mixed with the extract stream.

7. The process of claim 1 wherein the diluent recovered from the fourth separation column is mixed with the raffinate stream.

8. The process of claim 1 wherein the paraffins in the extract stream comprise normal and lightly branched paraffins in the C15 to C19 range.

9. The process of claim 1 wherein the diluent is a hydrocarbon in the C10 to C14 range selected from the group consisting of paraffins, naphthenes, aromatics and mixtures thereof.

10. The process of claim 1 wherein the diluent is a hydrocarbon in the C8 to C10 range selected from the group consisting of paraffins, naphthenes, aromatics and mixtures thereof.

11. The process of claim 10 wherein the diluent is a mixture comprising aromatics.

12. The process of claim 11 wherein the diluent is a mixture comprising paraxylene.

13. The process of claim 1 wherein the diluent is isooctane.

14. The process of claim 1 wherein the first desorbent is a hydrocarbon stream comprising hydrocarbons in the C5 to C8 range.

15. The process of claim 14 wherein the desorbent is a mixture of isooctane and either n-pentane or n-hexane.

16. The process of claim 1 wherein the second desorbent is a hydrocarbon stream comprising hydrocarbons in the C5 to C8 range.

17. The process of claim 16 wherein the second desorbent is a mixture of n-hexene and n-hexane.

18. The process of claim 1 wherein the operating conditions of the first separation column and second separation column include temperatures between 35° C. and 300° C., and pressures between 100 kPa and 500 kPa.

19. The process of claim 1 wherein the operating conditions of the third separation column and fourth separation column include temperatures between 35° C. and 300° C., and pressures between 10 kPa and 100 kPa.

* * * * *